United States Patent
Wang et al.

(10) Patent No.: US 10,024,815 B2
(45) Date of Patent: Jul. 17, 2018

(54) METHOD AND DEVICE FOR DETECTING PH VALUE OF A SOLUTION

(71) Applicant: KONINKLIJKE PHILIPS N.V., Eindhoven (NL)

(72) Inventors: Guangwei Wang, Eindhoven (NL); Peixin Hu, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 842 days.

(21) Appl. No.: 14/360,970

(22) PCT Filed: Nov. 30, 2012

(86) PCT No.: PCT/IB2012/056876
§ 371 (c)(1),
(2) Date: May 28, 2014

(87) PCT Pub. No.: WO2013/080182
PCT Pub. Date: Jun. 6, 2013

(65) Prior Publication Data
US 2014/0291171 A1 Oct. 2, 2014

(30) Foreign Application Priority Data
Dec. 2, 2011 (WO) ............... PCT/CN2011/083408

(51) Int. Cl.
*G01N 27/30* (2006.01)
*G01N 27/416* (2006.01)

(52) U.S. Cl.
CPC ....... *G01N 27/302* (2013.01); *G01N 27/4167* (2013.01)

(58) Field of Classification Search
None
See application file for complete search history.

(56) References Cited

U.S. PATENT DOCUMENTS 5,646,863 A * 7/1997 Morton ............... G01N 33/18
  210/688
6,541,617 B1 * 4/2003 Bamdad ............... B01J 13/00
  435/287.2

(Continued)

FOREIGN PATENT DOCUMENTS

CN   1493874 A   5/2004
JP   9113478 A   5/1997

(Continued)

OTHER PUBLICATIONS

Osaka T, et al: "Application of electroinactive polypyrrole film to the pH sensor electrode", Sensors and Actuators B: Chemical: International Journal Devoted to Research and Development of Physical and Chemical Transducers, Elsevier S.A. Switzerland, vol. 13, No. 1-3, May 1, 1993, pp. 205-208.

(Continued)

*Primary Examiner* — Jill A Warden
*Assistant Examiner* — Brittany I Fisher (57) ABSTRACT

A PH value detection device for detecting a PH value of a solution includes first and a second electrodes to be inserted into the solution; and a power source configured to apply a bipolar rectangular potential pulse signal to the first and second electrodes. A current detector is connected between the first and second electrodes and is configured to detect a current flowing through the first and second electrodes. A calculator is configured to calculate the PH value of the solution, based on the detected current.

11 Claims, 5 Drawing Sheets

(56) References Cited

U.S. PATENT DOCUMENTS

| | | | |
|---|---|---|---|
| 6,740,518 B1* | 5/2004 | Duong | G01N 27/3277 435/287.1 |
| 2003/0217919 A1 | 11/2003 | Yajima | |
| 2005/0001630 A1* | 1/2005 | Kaiser | G01N 27/221 324/453 |
| 2005/0017728 A1* | 1/2005 | Kaiser | G01N 27/221 324/453 |
| 2005/0244954 A1* | 11/2005 | Blackburn | B01L 3/502753 435/287.2 |
| 2008/0302660 A1* | 12/2008 | Kahn | A61B 5/14546 204/416 |
| 2009/0178923 A1* | 7/2009 | Marquant | A61B 5/14532 204/403.01 |
| 2009/0253149 A1* | 10/2009 | Ahrens | C12Q 1/003 435/7.4 |

FOREIGN PATENT DOCUMENTS

| JP | 2001153836 A | 6/2001 |
|---|---|---|
| WO | 02071047 A2 | 9/2002 |

OTHER PUBLICATIONS

Cox et al: "Square-wave amperometry", Journal of Electroanalytical Chemistry, Elsevier, Amsterdam, NL, vol. 136, No. 1, Jun. 10, 1982, pp. 93-104.

Patil P S et al: Electrochromism in spray deposited iridium oxide thin films:, Electrochimica Acta, Elsevier Science Publishers, Barking, GB, vo. 50, No. 12, Apr. 15, 2005, pp. 2527-2532.

Robert Long et al: "Spectral Imaging and Electrochemical Study on the Response Mechanism of Ionophore-Based Ploymeric Membrane Amperometric pH Sensors", Electroanalysis, vol. 15, No. 1516, Sep. 1, 2003, pp. 1261-1269.

Pasztor K et al: "Iridium oxide-based microelectrochemical transistors for pH sensing". Sensors and Actuators B: Chemical: International Journal Devoted to Research and Development of Physical and Chemical Transducers, Elsevier S.A., Switzerland, vol. 12, No. 3, Apr. 15, 1993, pp. 225-230.

* cited by examiner

METHOD AND DEVICE FOR DETECTING PH VALUE OF A SOLUTION

This application is the U.S. National Phase application under 35 U.S.C. § 371 of International Application No. PCT/IB2012/056876, filed on Nov. 30, 2012, which claims the benefit of Foreign Application No. PCT/CN2011/083408 filed on Dec. 2, 2011. These applications are hereby incorporated by reference herein.

FIELD OF THE INVENTION

The present invention relates to the field of PH value detection, more particularly, to a PH value detection device and a method of detecting a PH value.

BACKGROUND OF THE INVENTION

The PH is one of the most important parameters for characterizing the chemical properties of a solution. At present, the glass electrode is the most widely used sensor for detecting the PH value of the solution. In some special situations, e.g., in vivo applications, it is required that the PH sensor can be miniaturized, however, due to the fragility of the glass, the miniaturization of a PH sensor e.g., a glass electrode, is restricted. In addition, in some corrosive environments, e.g., in hydrofluoric acid solutions, the glass electrode does not respond properly to the PH detection.

The glass electrode is restricted in industrial application, and integrating it into home appliances is also very difficult because of a potential safety issue (frangibility of the glass), professional maintenance requirements, and short lifetime, etc.

On the other hand, the glass electrode is usually used as a working electrode in the prior art, and is used in co-operation with the reference electrode, e.g., an Ag/AgCl, saturated calomel electrode. Because calomel and the like are toxic and pollute the environment, it is better to avoid using the saturated calomel electrode. In addition, the use of the reference electrode also results in high cost and difficult maintenance of the electrode pair constituted by the glass electrode and the reference electrode.

Thus, there is an urgent need in the art to solve the above technical problems.

OBJECT AND SUMMARY OF THE INVENTION

Therefore, the present invention provides an improved PH value detection scheme, which is capable of solving or at least obviating part of the defects existing in the prior art.

According to the first aspect of the present invention, there is provided a PH value detection device, which device may comprise:

a first electrode and a second electrode, wherein the first electrode and the second electrode are to be inserted into a solution;

a power source for applying a bipolar rectangular potential pulse signal to the first electrode and the second electrode;

a current detection means connected between the first electrode and the second electrode for detecting a current I flowing through the first electrode and the second electrode; and a calculating unit for calculating the PH value of the solution, based on the detected current I.

In an embodiment of the present invention, the first electrode may comprise a transition metal/transition metal oxide electrode, and the second electrode may comprise an inert electrode. The transition metal/transition metal oxide electrode can be selected from e.g., an $Ag/Ag_2O$ electrode, $W/WO_3$ electrode, $Mn/MnO$ electrode or $Ir/IrO_2$ electrode, and the inert electrode can be selected from e.g., a Cu electrode, Pt electrode, Au electrode or stainless steel electrode. Preferably, the transition metal/transition metal oxide electrode is an $Ag/Ag_2O$ electrode, and the inert electrode is a stainless steel electrode.

In a further embodiment of the present invention, the PH value detection device of the present invention may comprise a storing unit for pre-storing a function which correlates the current I and the PH value. Alternatively, the storing unit pre-stores a plurality of functions correlating the current I and the PH value, each function being associated with the type of solution to be detected.

Alternatively, the PH value detection device may further comprise a user interface for receiving data reflecting the type of solution to be detected for selecting a function from said plurality of functions.

Alternatively, the calculating unit can calculate the PH value of the solution to be detected according to the detected current I and the pre-stored function.

According to the second aspect of the present invention, there is provided a method of detecting a PH value, which method may comprise:

applying a bipolar rectangular potential pulse signal to a first electrode and a second electrode inserted into the solution;

detecting a current I flowing through the first electrode and the second electrode; and calculating the PH value of the solution, based on the detected current I.

In an embodiment of the present invention, the first electrode may comprise a transition metal/transition metal oxide electrode, and the second electrode may comprise an inert electrode. The transition metal/transition metal oxide electrode can be selected from e.g., an $Ag/Ag_2O$ electrode, $W/WO_3$ electrode, $Mn/MnO$ electrode or $Ir/IrO_2$ electrode, and the inert electrode can be selected from e.g., a Cu electrode, Pt electrode, Au electrode or stainless steel electrode.

In a further embodiment of the present invention, the method of detecting a PH value according to the present invention may further comprise pre-storing a function which correlates the current I and the PH value. Alternatively, a plurality of functions correlating the current I and the PH value can be pre-stored, each function being associated with the type of solution to be detected.

Alternatively, the method of detecting a PH value according to the present invention may further comprise receiving data reflecting the type of solution to be detected from a user interface for selecting a function from said plurality of functions.

Alternatively, the method for detecting a PH value according to the present invention may further comprise calculating the PH value of the solution to be detected, based on the detected current I and the pre-stored function.

By means of the above design of the present invention, the use of the fragile glass electrode and the reference electrode, e.g., an Ag/AgCl saturated calomel electrode, can be avoided, which has a favorable effect on the daily maintenance of the PH value detection device and on the protection of the environment, and it also has a favorable effect on the miniaturization and facilitation of the PH value detection device. In addition, only measuring the current flowing through the electrode pair (constituted by the first electrode and the second electrode) to calculate the PH value of the solution to be detected brings many conveniences, which facilitate real time monitoring of the change of the PH value of the solution, thereby bringing many unexpected advantages to, inter alia, the field of industrial production.

DETAILED DESCRIPTION OF EMBODIMENTS

The present invention will be described hereinafter in detail with reference to the accompanying drawings and the exemplary embodiment(s).

Firstly, the principle of the present invention is introduced as follows:

In electrochemistry, the working electrode and the counter electrode are usually used to measure the PH value of a solution. For example, in the case that the $Ag/Ag_2O$ electrode is used as the working electrode and the Pt electrode is used as the counter electrode, and that a bipolar rectangular potential pulse signal is applied to the working electrode and the counter electrode, the following reaction will occur:

When the $Ag/Ag_2O$ electrode acts as an anode:
$$2Ag+H_2O-2e \rightarrow Ag_2O+2H^+; \quad (1)$$

When the $Ag/Ag_2O$ electrode acts as a cathode:
$$Ag_2O+2H^-+2e \rightarrow 2Ag+H_2O \quad (2)$$

Based on the above reaction, the potential change of the $Ag/Ag_2O$ electrode can be calculated according to the following formula:

For example, when the $Ag/Ag_2O$ electrode works as an anode, the reaction as shown in formula (1) occurs, $$\varphi(Ag/Ag_2O) = \varphi^\Phi(Ag/Ag_2O) + \frac{0.0591}{2} lg \frac{[Ag_2O][H^+]^2}{[Ag]^2}, \quad (3)$$

Supposing that $[Ag] \approx 1$, $[Ag_2O] \approx 1$, then, said equation (3) can be approximately:

$$\varphi(Ag/Ag_2O)=\varphi^\Phi(Ag/Ag_2O)+0.0591 \, lg[H^+]=\varphi^\Phi(Ag/Ag_2O)-0.0591 PH \quad (4)$$

It can be seen from formula (4) that the PH value of the solution can be obtained from the potential change of the $Ag/Ag_2O$ electrode. During the reaction process between the $Ag/Ag_2O$ electrode surface and the solution, the potential change of the $Ag/Ag_2O$ electrode will be superposed together with an external voltage applied on the working electrode and the counter electrode. Supposing that the external voltage does not change, since the oxidation reaction occurs on the surface of the $Ag/Ag_2O$ electrode (when the $Ag/Ag_2O$ electrode works as a cathode, a reducing reaction will occur on the surface of the $Ag/Ag_2O$ electrode, as shown in formula (2)), the potential between the $Ag/Ag_2O$ electrode surface and the solution is changed. Supposing that the impedance of the solution is not changed, then the current I flowing through the working electrode and the counter electrode will be changed with the change of the potential between the $Ag/Ag_2O$ electrode surface and the solution. Therefore, the change of the potential of the $Ag/Ag_2O$ electrode can be reflected by the captured current I that flows through the working electrode and the counter electrode. The present invention is designed exactly on the basis of the above principle.

After the introduction of the principle of the present invention, the Partial Least Squares Regression (PLSR) used in the present invention will be described below.

It can be seen from the above description of the principle of the present invention that the potential change between the surface of the working electrode e.g., an $Ag/Ag_2O$ electrode, and the solution can be reflected by the captured current I that flows through the working electrode and the counter electrode, and that there is a linear relation (as shown in formula (4)) between the potential change between the $Ag/Ag_2O$ electrode surface and the solution $\varphi(Ag/Ag_2O)-\varphi^\Phi(Ag/Ag_2O)$ and the PH value of the solution and, hence, there is also a linear relation between the current I that flows through the working electrode and the counter electrode and the PH value of the solution. Based on the linear relation between the latter two, use can be made of the Partial Least Squares Regression to process the related data, the processing procedure being introduced as follows:

Supposing that X is an input vector of the characteristic value of the current I, i.e., $\{x_0 \ldots x_n\}$, that Y is an output value representing the PH value of e.g., the water calibration solution and that there is a linear relation between Y and X:

$$Y=XB+g \quad (5)$$

wherein, B is vector $\{b_0 \ldots b_n\}$, and g is a coefficient. The vector B to be determined and the coefficient g in the functional formula (5) can be predetermined by using e.g., the water calibration solution, so as to determine the linear relation between Y representing the PH value and the input vector X representing the characteristic value of the current I. For example, in the case that the inventor has learned several (as many as possible, generally more than 6) PH values of the water calibration solution, the sample data $x_0 \ldots x_n$ of the current flowing through the working electrode and the counter electrode is obtained from measurements at different time sampling points. These data are entered into the functional formula (5) to obtain:

$$\begin{bmatrix} x_{00} & \cdots & x_{0n} \\ \vdots & \ddots & \vdots \\ x_{m0} & \cdots & x_{mn} \end{bmatrix} \begin{bmatrix} b_0 \\ \vdots \\ b_n \end{bmatrix} + g = y \quad (6)$$

The minimum variance of the data can be obtained by optimizing B and g. In the present invention, the inventor uses the Matlab function: plsregress (X, Y) to optimize B and g. Alternatively, the skilled person in the art can also use other mathematic software such as Maple, Mathematica to optimize B and g. It is not difficult for the person skilled in the art to use the optimized function, based on the acquired knowledge or related textbooks; therefore, this will not be explained in detail here.

The inventor can substitute the sample data $x_0^a \ldots x_m^a$ of the current I obtained for the solution to be detected, in the formula (5), to calculate the PH value of the solution to be detected by using the functional formula (5) with the optimized B and g. This calculated PH value can serve as the predicted value of the solution to be detected. The inventor then fits the calculated PH value for the solution to be detected with the actually measured PH value, finding that there is a relatively small deviation between the calculated PH value and the actually measured PH value. Therefore, it is further proved that the purpose of predetermining the linear relation (i.e., determining B and g) between Y representing the PH value and the input vector X representing the characteristic value of the current I, and then calculating the PH value of the solution to be detected by means of the measured current I that flows through the electrode pair, as assumed by the inventor, is tenable.

The relevant experiments performed by the inventor of the present invention are introduced hereinafter.

Figure 3:
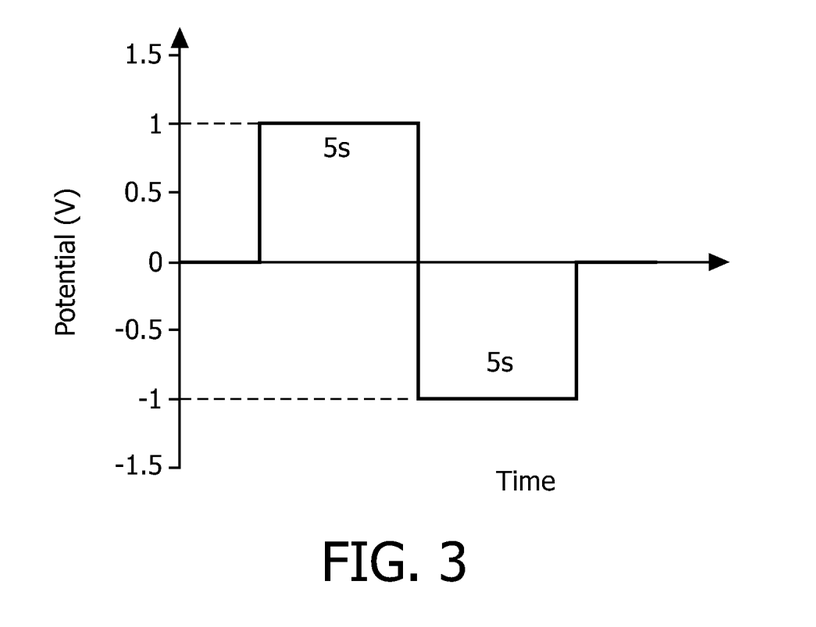
FIG. 3 schematically shows a bipolar rectangular potential pulse signal used in the present invention.

The inventor uses the Ag/Ag$_2$O electrode as the working electrode, and the stainless steel electrode as the counter electrode, and the calibration solution is water. The bipolar rectangular potential pulse signal as shown in FIG. 3 is applied on the Ag/Ag$_2$O electrode and the stainless steel electrode, after which the current I that flows through the Ag/Ag$_2$O electrode and the stainless steel electrode is measured at twelve time sampling points 0 s, 1 s, 2 s, 3 s, 4 s, 4.9 s, 5.1 s, 6 s, 7 s, 8 s, 9 s, 10 s. The six groups of experimental data measured by the inventor are listed in Table 1:

For example, in the first group of experiments, in the case that the PH value of the water calibration solution is 4.14, and the sampling time points are 0 s, 1 s, 2 s, 3 s, 4 s, 4.9 s, 5.1 s, 6 s, 7 s, 8 s, 9 s, 10 s, the measured currents that flow through the Ag/Ag$_2$O electrode and the stainless steel electrode are 459.375, 51.27159 . . . −37.4951. For example, in the second group of experiments, in the case that the PH value of the water calibration solution is 5.68, and the sampling time points are 0 s, 1 s, 2 s, 3 s, 4 s, 4.9 s, 5.1 s, 6 s, 7 s, 8 s, 9 s, 10 s, the measured currents that flow through the Ag/Ag$_2$O electrode and the stainless steel electrode are 464.05, 33.1067 . . . −28.6738. As for the data of the third to sixth groups of experiments, reference is made to Table 1. Then the six groups of data in Table 1 are substituted into the functional formula (5), the minimum variance of the data can be obtained by optimizing B and g. Therefore, B and g are determined. The obtained values for B are listed in Table 2:

TABLE 2

| | B |
|---|---|
| b0 | 0.048889924 |
| b1 | −0.04036251 |
| b2 | 0.105352896 |
| b3 | 0.142525159 |
| b4 | 0.142602611 |
| b5 | 0.130764991 |
| b6 | 0.035473844 |
| b7 | 0.199656442 |
| b8 | 0.019698151 |
| b9 | −0.00752623 |
| b10 | −0.00778502 |
| b11 | −0.00772294 |

The obtained coefficient g=21.123.

Figure 4:
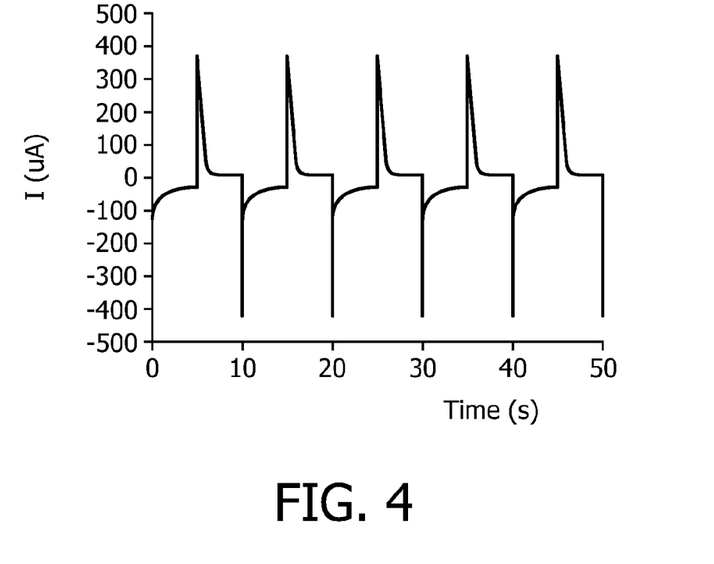
FIG. 4 schematically shows a current response measured in the present invention.
Figure 5:
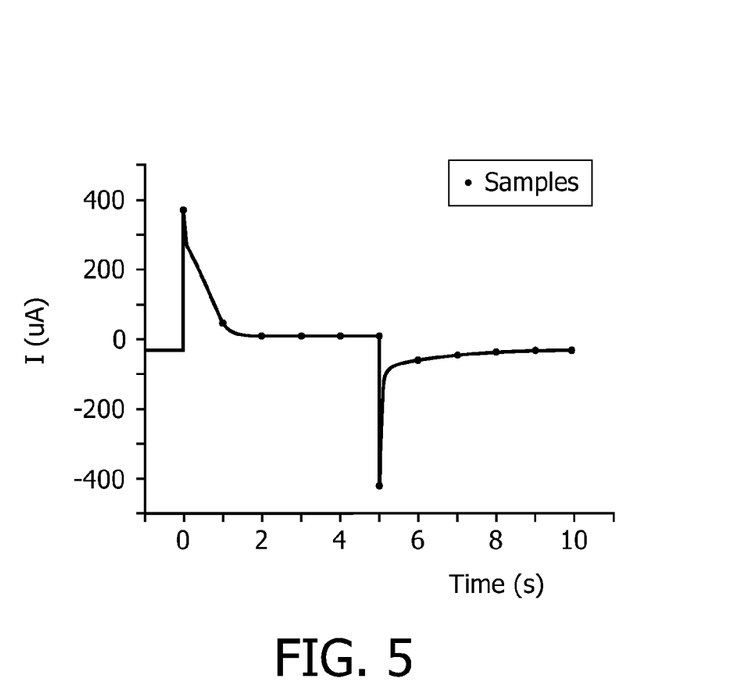
FIG. 5 schematically shows characteristic points of the current response for Partial Least Squares Regression (PLSR).

After the values for B and g in the functional formula (5) are determined, the linear relation between X representing the characteristic points of the measured current I and Y representing the PH value of the solution to be detected is also determined. As for the solution to be detected, e.g., a Na$_2$HPO$_4$ buffer solution, the values X{x$_0$, x$_1$ . . . x$_{11}$} of the characteristic points of the current I that flows through the Ag/Ag$_2$O electrode and the stainless steel electrode are obtained by sampling at the time sampling points 0 s, 1 s, 2 s, 3 s, 4 s, 4.9 s, 5.1 s, 6 s, 7 s, 8 s, 9 s, 10 s, after which the corresponding PH values can be calculated. FIG. 4 schematically shows the current response measured in the experiments, i.e., a curve of the change of the current I that flows through the Ag/Ag$_2$O electrode and the stainless steel electrode with respect to time. Here the inventor measures the current response of five periods, each period is 10 s. FIG. 5 schematically shows the characteristic points of the current response for the Partial Least Squares Regression (PLSR),

TABLE 1

| | pH | | | | | |
|---|---|---|---|---|---|---|
| sampling time | 4.14 | 5.68 | 6.54 | 7.81 | 8.93 | 9.83 |
| 0 s | 459.375 | 464.05 | 493.3875 | 484 | 502.0375 | 476.025 |
| 1 s | 51.27159 | 33.1067 | 31.85023 | 26.09739 | 22.96114 | 23.71239 |
| 2 s | 21.09898 | 14.49523 | 13.74091 | 11.97023 | 11.65932 | 11.04886 |
| 3 s | 15.08205 | 10.58545 | 10.32875 | 9.391466 | 9.400375 | 8.686341 |
| 4 s | 13.16091 | 8.941591 | 8.845989 | 8.180568 | 8.273705 | 7.6135 |
| 4.9 s | 11.35716 | 8.241386 | 8.145909 | 7.50558 | 7.63658 | 7.007432 |
| 5.1 s | −471.663 | −472.588 | −504.313 | −497.175 | −511.763 | −487.813 |
| 6 s | −73.1394 | −56.0642 | −53.8794 | −47.0853 | −42.9628 | −42.5068 |
| 7 s | −57.0983 | −42.7143 | −39.4809 | −33.521 | −29.2886 | −28.2759 |
| 8 s | −47.368 | −35.5136 | −32.1443 | −26.891 | −22.8959 | −21.861 |
| 9 s | −41.0259 | −31.0949 | −27.7693 | −22.8916 | −19.1939 | −18.2167 |
| 10 s | −37.4951 | −28.6738 | −25.4182 | −20.6586 | −17.2081 | −16.2645 | wherein the inventor intercepts twelve characteristic points in one period, as represented by the small circles in the figure. The time sampling points with which the twelve characteristic points correspond are 0 s, 1 s, 2 s, 3 s, 4 s, 4.9 s, 5.1 s, 6 s, 7 s, 8 s, 9 s, 10 s respectively. For the convenience of calculation, the inventor intercepts the curve of the current response from 5 s to 15 s in FIG. 4 as one period, and starts to calculate the time from 0 s of the intercepted period, as shown in the time segment from 0 s to 10 s in FIG. 5.

Figure 6A:
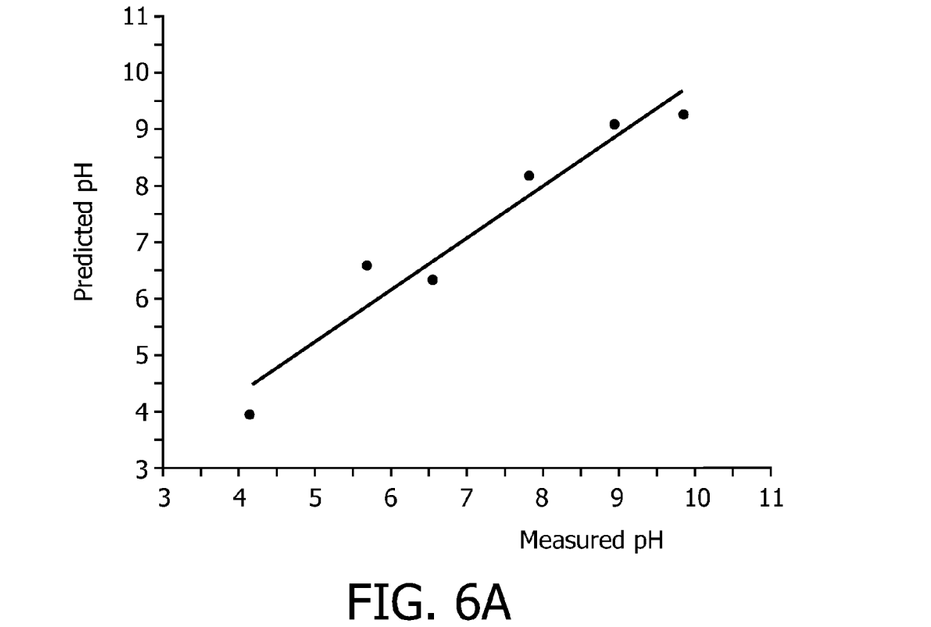
FIG. 6A schematically shows a fitting relation between the predicted PH value obtained from PLSR calculation and the experimental PH value, wherein the $Ag/Ag_2O$ electrode is used as the working electrode, and the stainless steel electrode is used as the counter electrode.

FIG. 6A shows a fitting relation between the predicted PH value obtained from PLSR calculation and the PH value measured in the experiments by taking the $Na_2HPO_4$ buffer solution as the solution to be detected. For example, when the calculated PH value (predicted PH value) is 3.9, the actually measured PH value (measured PH value) is 4.1; when the predicted PH value is 6.6, the measured PH value is 5.7; when the predicted PH value is 6.2, the measured PH value is 6.5; when the predicted PH value is 8.1, the measured PH value is 7.8; when the predicted PH value is 8.9, the measured PH value is 8.8; when the predicted PH value is 9.1, the measured PH value is 9.7. There is a deviation between the predicted PH value and the measured PH value because the PH value of the water calibration solution used and the PH value of the solution to be detected do not exactly match, such that there is a deviation between the determined B and g in the functional formula (5) and the actual situation. The deviation between the predicted PH value and the measured PH value may be caused by the experimental conditions; what can be learned by the person skilled in the art is that in some situations in which the PH value detection is not required to be very accurate, the PH value detection device of the present invention is sufficient to replace the glass electrode and the reference electrode used in the prior art.

Figure 6B:
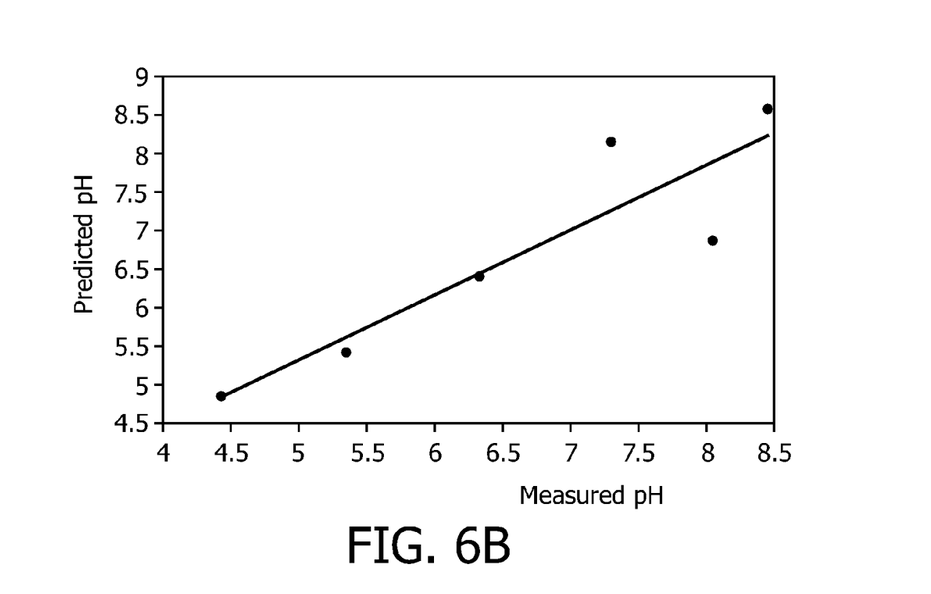
FIG. 6B schematically shows a fitting relation between the predicted PH value obtained from PLSR calculation and the experimental PH value, wherein the $W/WO_3$ electrode is used as the working electrode, and the stainless steel electrode is used as the counter electrode.

FIG. 6B shows a fitting relation between the predicted PH value obtained from PLSR calculation and the PH value measured in the experiments in the case that the inventor uses the $W/WO_3$ electrode as the working electrode, the stainless steel electrode as the counter electrode, and other experimental conditions are the same as those in FIG. 6A.

It shall be pointed out that the above calibration solutions used by the inventor are six kinds of water calibration solutions (as many as possible for increasing accuracy), each water calibration solution has a corresponding PH value, for instance, the PH value of the first kind of water calibration solution is 4.14, and the PH value of the second kind of water calibration solution is 5.68, . . . as shown in Table 1. The person skilled in the art shall understand that other calibration solutions with determined PH values can also be used in the application of the present invention, as long as the PH value range of the plurality of selected calibration solutions covers the PH value range of the solution to be detected. For example, if the PH value range of the solution to be detected may be 5-8, then the PH value range of the various selected calibration solutions can be 4-9, because the PH value range 4-9 covers the PH value range 5-8.

Although the solution to be detected used in the embodiments of the present invention is the $Na_2HPO_4$ buffer solution, it is easy for the person skilled in the art to understand that the PH value detection device of the present invention is not limited to detecting the PH value of the $Na_2HPO_4$ buffer solution. The PH value detection device of the present invention can be applied in many industrial or home applications in which real time monitoring of PH values is required.

In FIG. 6A, the PH value range of the six kinds of water calibration solutions ranges from 4-9 to perform experiments, thereby determining the linear function applicable for the solution to be detected with a PH value in the range of 4-9, said function correlating the relation between X representing the characteristic points of the measured current I and Y representing the PH value of the solution to be detected. The person skilled in the art should understand that as for other PH value ranges, such as 1-3 or 10-14, the above experiments should also be repeated to determine the corresponding B and g, thereby determining the linear function applicable for this PH value range.

Since the determination of B and g in the functional formula (5) is associated with the electrode pair used and the calibration solution selected (i.e., selected PH value range), when the user selects different electrode pairs and different calibration solutions (with different PH value ranges), different functional formulae will be obtained when B and g are determined by the calibration solution with a known PH value and by measuring the current flowing through the selected electrode pair, which is not difficult to understand for the person skilled in the art. For example, if the user selects the $Ag/Ag_2O$ electrode as the working electrode, the stainless steel electrode as the counter electrode, and six kinds of water calibration solutions with PH values in the range of 4-9 for calibration (each kind of the water calibration solution has a certain PH value), the linear function $Y_1=X_1B_1+g_1$ between X representing the characteristic points of the measured current I and Y representing the PH value of the solution to be detected is obtained, for example, the B vector {b0, b1 . . . b11} and the corresponding, determined g=21.123 shown in Table 2 are indicated as $B_1$, $g_1$ herein. If the user changes the working electrode, and selects the Mn/MnO electrode as the working electrode, the stainless steel electrode as the counter electrode, and six kinds of water calibration solutions with a PH value in the range of 4-9 for calibration (as shown in FIG. 6B), the linear function $Y_2=X_2B_2+g_2$ is obtained, wherein $B_2$, $g_2$ might be different from $B_1$, $g_1$, hence, the functional formula $Y_2=X_2B_2+g_2$ might be different from the functional formula $Y_1=X_1B_1+g_1$. If the user still selects the $Ag/Ag_2O$ electrode as the working electrode, and the stainless steel electrode as the counter electrode, while changing the calibration solution, for example, by selecting six kinds of alkaline solutions with a PH value in the range of 8-11 as the calibration solutions for calibration (each kind of the alkaline solutions has a certain PH value), the linear function $Y_3=X_3B_3+g_3$ is obtained, wherein $B_3$, $g_3$ might be different from both $B_1$, $g_1$ and $B_2$, $g_2$, hence, the functional formula $Y_3=X_3B_3+g_3$ might be different from both the functional formula $Y_1=X_1B_1+g_1$ and the functional formula $Y_2=X_2B_2+g_2$, which is not difficult to understand for the person skilled in the art.

The figures of the present invention will be described hereinafter.

Figure 1:
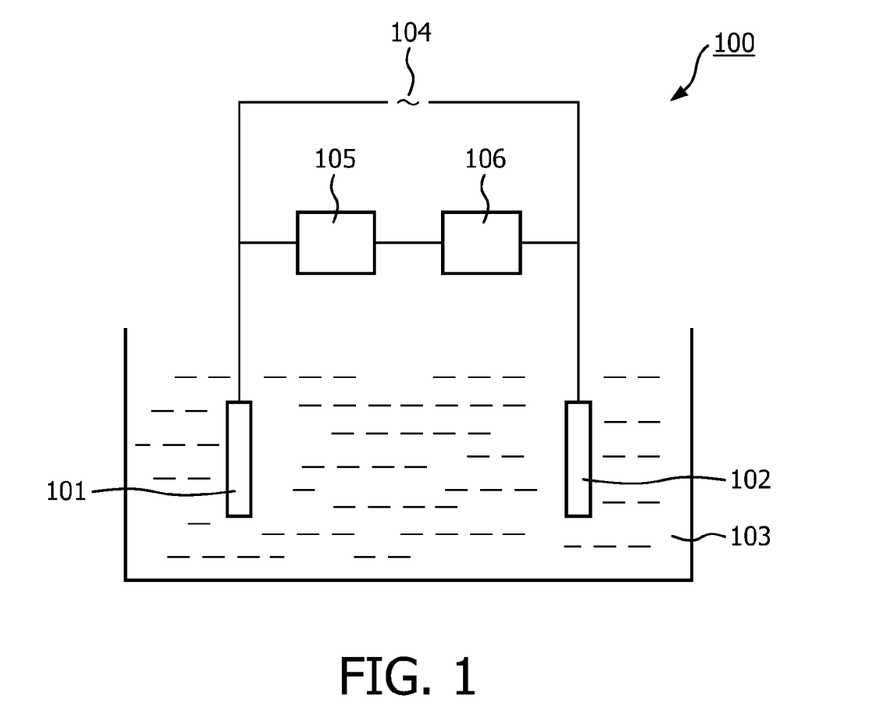
FIG. 1 schematically shows a PH value detection device according to one aspect of the present invention.

FIG. 1 schematically shows a PH value detection device 100 according to one aspect of the present invention, which may comprise: a first electrode 101 and a second electrode 102, wherein the first electrode 101 and the second electrode 102 are to be inserted into a solution to be detected 103. When the first electrode 101 is used as the working electrode, the second electrode 102 is used as the counter electrode. The person skilled in the art can understand that when the first electrode 101 is used as the counter electrode, the second electrode 102 is used as the working electrode. In the embodiments of the present invention, various situations in which the first electrode 101 is used as the working electrode are given. In order to avoid using the glass electrode, the first electrode 101 of the present invention may comprise a transition metal/transition metal oxide electrode, e.g., an Ag/Ag$_2$O electrode, W/WO$_3$ electrode, Mn/MnO electrode or Ir/IrO$_2$ electrode, etc. The second electrode 102 of the present invention may comprise the inert electrode, e.g., a Cu electrode, Pt electrode, Au electrode or stainless steel electrode, etc. In the embodiments of the present invention, the solution to be detected can be water, Na$_2$HPO$_4$ buffer solution or various other solutions whose PH values have to be detected (?).

The PH value detection device 100 of the present invention may further comprise a power source 104 for applying a bipolar rectangular potential pulse signal to the first electrode 101 and the second electrode 102. FIG. 3 schematically shows the bipolar rectangular potential pulse signal used in the present invention; the amplitude of the bipolar rectangular potential pulse signal is ±1V, and the period of the pulse is 10 s. The person skilled in the art should understand that the present invention is also suitable for other bipolar rectangular potential pulses with an amplitude of ±2V and a pulse period of 10 s, or with an amplitude of ±1V and a pulse period of 20 s, etc. Thus, the pulse waveform in FIG. 3 is only schematic, the present invention is not limited thereto.

The PH value detection device 100 of the present invention may further comprise current detection means 105 connected between the first electrode 101 and the second electrode 102 for detecting a current I flowing through the first electrode 101 and the second electrode 102.

Figure 2A:
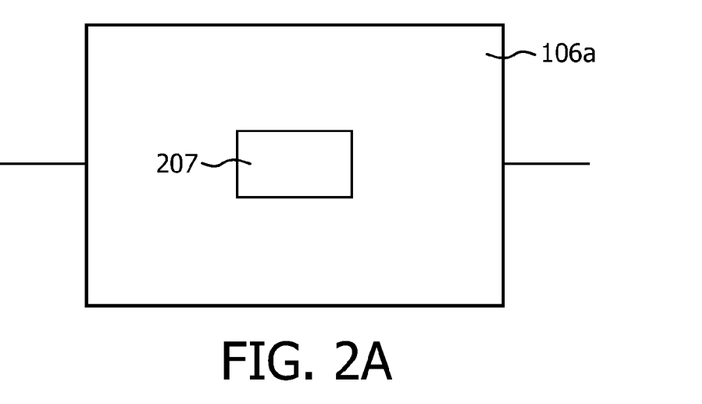
FIG. 2A schematically shows a layout chart of a storing unit and a calculating unit according to an embodiment of the present invention.

The PH value detection device 100 of the present invention may further comprise a calculating unit 106 for calculating the PH value of the solution to be detected, based on the detected current I. In an embodiment of the present invention, the calculating unit 106 may be a calculating unit comprising a storing unit 207, i.e., the storing unit 207 is integrated with the calculating unit 106; FIG. 2A exactly shows the situation in which the storing unit 207 is integrated with the calculating unit 106a. Alternatively, the storing unit 207 may also be an individual unit, i.e., the storing unit 207 and the calculating unit 106a are two individual units (not shown). The storing unit 207 can pre-store a function associated with the current I and the PH value, e.g., PH=BI+g, which function is similar to a linear function between X representing the characteristic points of the measured current I and Y representing the PH value of the solution to be detected as shown in the functional formula (5), and the vector B and the coefficient g therein are determined. The calculating unit 106a calculates the PH value of the solution to be detected, based on the detected current I and the pre-stored function PH=BI+g. Alternatively, the storing unit 207 can pre-store a plurality of functions, each function correlating the current I and the PH value associated with the type of solution to be detected. For example, the functions PH=IB$_1$+g$_1$; PH=IB$_2$+g$_2$; PH=IB$_3$+g$_3$; PH=IB$_4$+g$_4$; PH=IB$_5$+g$_5$ associated with the types of solution to be detected, i.e., strong acidity, sub-acidity, neutrality, slightly alkaline, strong basicity, can be pre-stored in the storing unit 207, wherein B$_1$, g$_1$, B$_2$, g$_2$, B$_3$, g$_3$, B$_4$, g$_4$, B$_5$, g$_5$ are determined according to the Partial Least Squares Regression introduced above, so, the linear functional relations between the current I and the PH value in the functions PH=IB$_1$+g$_1$; PH=IB$_2$+g$_2$; PH=IB$_3$+g$_3$; PH=IB$_4$+g$_4$; PH=IB$_5$+g$_5$ are also determined.

Figure 2B:
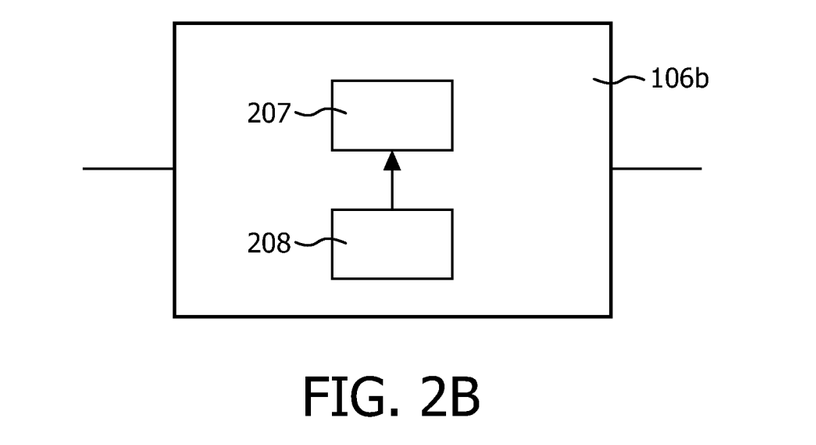
FIG. 2B schematically shows a layout chart of a storing unit, a user interface and a calculating unit according to another embodiment of the present invention.

In an embodiment of the present invention, the PH value detection device 100 of the present invention may further comprise a user interface 208 for receiving, from a user, data reflecting the type of solution to be detected to select a function from said plurality of functions. For example, if the solution to be detected is tap water, the user can directly input or select "neutrality" on the user interface 208 of e.g., a soft keypad or a liquid crystal touch panel as the type of solution to be detected, and the function that corresponds to tap water as the type of the solution to be detected is PH=IB$_3$+g$_3$. If the solution to be detected is edible vinegar, the user can directly input or select "sub-acidity" on the user interface 208 of e.g., a soft keypad or a liquid crystal touch panel as the type of solution to be detected, and the function that corresponds to the edible vinegar as the type of solution to be detected is PH=IB$_2$+g$_2$. Then, a calculating unit 106b calculates the PH value of the solution to be detected, based on the detected current I and the pre-stored function (i.e., a function selected from the five functions). The above situation is shown in FIG. 2B.

The person skilled in the art should learn that the above types of solution to be detected, i.e., strong acidity, sub-acidity, neutrality, slightly alkaline, strong basicity, and the five corresponding functions PH=IB$_1$+g$_1$; PH=IB$_2$+g$_2$; PH=IB$_3$+g$_3$; PH=IB$_4$+g$_4$; PH=IB$_5$+g$_5$ are only schematic, i.e. the present invention is not limited to the above types of solution to be detected and functions, and the person skilled in the art can make various modifications, such as designing three types of solution to be detected and three corresponding functions, so as to simplify the operating steps; or designing more types of solution to be detected and more corresponding functions, so as to subdivide the types of solution to be detected more specifically.

Figure 7:
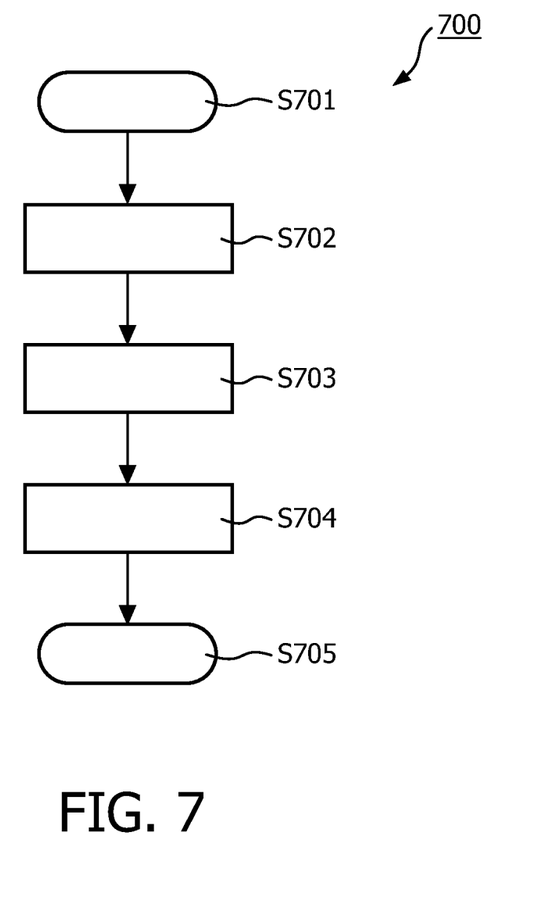
FIG. 7 schematically shows a flow chart of the method of detecting a PH value according to another aspect of the present invention.

Now, referring to FIG. 7, said figure schematically shows a flow chart of the method 700 of detecting a PH value according to another aspect of the invention. The method in FIG. 7 starts from S701, and after that, in S702, a bipolar rectangular potential pulse signal is applied to a first electrode 101 and a second electrode 102 inserted into a solution to be detected, so as to stimulate the potential reaction on the first electrode 101. The first electrode 101 may comprise a transition metal/transition metal oxide electrode, and the second electrode 102 may comprise an inert electrode. The transition metal/transition metal oxide electrode can be selected from an Ag/Ag$_2$O electrode, W/WO$_3$ electrode, Mn/MnO electrode or Ir/IrO$_2$ electrode, and the inert electrode can be selected from a Cu electrode, Pt electrode, Au electrode or stainless steel electrode. Then, in S703, a current I flowing through the first electrode 101 and the second electrode 102 is detected. Finally, the PH value of the solution to be detected is calculated based on the detected current I. Alternatively, a function which correlates the current I and the PH value can be pre-stored in the storing unit 207 before detecting the current I flowing through the first electrode 101 and the second electrode 102 in S703, for example, being pre-stored in the storing unit 207 by the manufacturer or by the user according to the instruction of the user's manual. This pre-storing step can be performed either before step S702 or after step S702 and before step S703.

Alternatively, a plurality of functions can be pre-stored, for example, in the storing unit 207 by the manufacturer or by the user according to the instruction of the user's manual. This pre-storing step can be performed either before step S702 or after step S702 and before step S703. Each of the plurality of functions correlates the current I and the PH value associated with the type of solution to be detected. For example, the functions PH=IB$_1$+g$_1$; PH=IB$_2$+g$_2$; PH=IB$_3$+g$_3$; PH=IB$_4$+g$_4$; PH=IB$_5$+g$_5$ associated with the types of solution to be detected, i.e., strong acidity, subacidity, neutrality, slightly alkaline, strong basicity, can be pre-stored in the storing unit 207, wherein $B_1$, $g_1$, $B_2$, $g_2$, $B_3$, $g_3$, $B_4$, $g_4$, $B_5$, $g_5$ are determined according to the Partial Least Squares Regression introduced above, so that, the linear functional relations between the current I and the PH value in the functions $PH=IB_1+g_1$; $PH=IB_2+g_2$; $PH=IB_3+g_3$; $PH=IB_4+g_4$; $PH=IB_5+g_5$ are also determined.

In another embodiment of the present invention, the method 700 of detecting the PH value may further comprise receiving data reflecting the type of solution to be detected from a user interface for selecting a function from said plurality of functions. This step can be performed after pre-storing the plurality of functions and before applying the bipolar rectangular potential pulse signal to the first electrode 101 and the second electrode 102. For example, if the solution to be detected is tap water, the user can directly input or select "neutrality" on the user interface 208 of e.g., a soft keypad or a liquid crystal touch panel as the type of solution to be detected, and the function that corresponds to the tap water as the type of solution to be detected is PH=IB3+g3. If the solution to be detected is edible vinegar, the user can directly input or select "sub-acidity" on the user interface 208 of e.g., a soft keypad or a liquid crystal touch panel as the type of solution to be detected, and the function that corresponds to the edible vinegar as the type of solution to be detected is PH=IB2+g2. Then in step S704, a calculating unit 106b calculates the PH value of the solution to be detected, based on the detected current I and the pre-stored function (i.e., a function selected from the five functions), and the method end in step S705.

Similarly, in the method 700 for detecting the PH value of the present invention, the above types of solution to be detected, i.e., strong acidity, sub-acidity, neutrality, slightly alkaline, strong basicity, and the five corresponding functions $PH=IB_1+g_1$; $PH=IB_2+g_2$; $PH=IB_3+g_3$; $PH=IB_4+g_4$; $PH=IB_5+g_5$ are only schematic, the present invention is not limited to the above types of solution to be detected and functions, i.e. the person skilled in the art can make various modifications, such as designing three types of solution to be detected and three corresponding functions, so as to simplify the operating steps; or designing more types of solution to be detected and more corresponding functions, so as to subdivide the types of solution to be detected more specifically.

By means of the above design of the present invention, the use of the fragile glass electrode and the reference electrode of e.g., an Ag/AgCl calomel electrode, can be avoided, which has a favorable effect on the daily maintenance of the PH value detection device and on the protection of the environment, and it also has a favorable effect on the miniaturization and facilitation of the PH value detection device. In addition, only measuring the current flowing through the electrode pair to calculate the PH value of the solution to be detected brings many conveniences, which facilitate real time monitoring of the change of the PH value of the solution, thereby bringing many unexpected advantages to, inter alia, the field of industrial production.

Although the present invention has been described with reference to currently considered embodiments, it should be understood that the present invention is not limited to the embodiments as disclosed. In contrast, the present invention aims to cover various modifications and equivalent arrangements involved in the spirit and scope of the appended claims. The scope of the following claims conforms to the widest interpretation so as to include all such modifications as well as equivalent structures and functions.

The above mentioned calculating unit can be implemented by way of software, hardware or combinations thereof. For example, it can be implemented by software and the program codes performing the calculating function are stored in a memory and are loaded and executed by a micro controller unit (MCU). Those skilled in the art could implement embodiments of the invention in various ways according to the concept and principle taught by the description. In the claims, the word "comprising" does not exclude other elements or steps, and the indefinite article "a" or "an" does not exclude a plurality. A single unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A PH value detection device for detecting the PH value of a solution, comprising:
   a first electrode and a second electrode, wherein the first electrode and the second electrode are configured to be inserted into the solution, the first electrode comprises a transition metal/transition metal oxide electrode, and the second electrode comprises an inert electrode;
   a power source configured to apply a bipolar rectangular potential pulse signal to the first electrode and the second electrode;
   a current detector connected between the first electrode and the second electrode and configured to detect a current flowing through the first electrode and the second electrode;
   a memory configured to pre-store a plurality of functions correlating current and PH values for a plurality of solution types, each function of the plurality of functions being associated with a type of solution to be detected; and
   a calculator configured to calculate the PH value of the solution, based on the detected current and the plurality of functions stored in the memory,
   wherein the plurality of functions are linear functions having slopes and y-intercepts which are determined using a plurality of types of solutions having different PH values that are in a first range, the first range being larger than a second range of PH values that includes the PH value of the solution to be detected.

2. The device as claimed in claim 1, wherein the transition metal/transition metal oxide electrode is selected from an Ag/Ag$_2$O electrode, W/WO$_3$ electrode, Mn/MnO electrode or Ir/IrO$_2$ electrode, and the inert electrode is selected from a Cu electrode, Pt electrode, Au electrode or stainless steel electrode.

3. The device as claimed in claim 1, further comprising a user interface configured to receive data reflecting the type of solution to be detected to select a pre-stored function from said plurality of functions associated with the type of solution to be detected.

4. The device as claimed in claim 3, wherein the calculating unit is configured to calculate the PH value of the solution to be detected according to the detected current and the selected pre-stored function.

5. The device of claim 1, wherein the plurality of functions include a pre-stored function which is a linear function having a slope and a y-intercept which are determined using a type of solution having a PH value approximate to the PH value of the solution to be detected.

6. A method of detecting a PH value of a solution, comprising acts of:
   applying a bipolar rectangular potential pulse signal to a first electrode and a second electrode inserted into the solution, wherein the first electrode comprises a transition metal/transition metal oxide electrode, and the second electrode comprises an inert electrode;

detecting a current flowing through the first electrode and the second electrode;

calculating the PH value of the solution, based on the detected current; and pre-storing a plurality of functions correlating current and PH values for a plurality of solution types, each function of the plurality of functions being associated with a type of solution to be detected.

7. The method as claimed in claim 6, wherein the transition metal/transition metal oxide electrode is selected from an $Ag/Ag_2O$ electrode, $W/WO_3$ electrode, $Mn/MnO$ electrode or $Ir/IrO_2$ electrode, and the inert electrode is selected from a Cu electrode, Pt electrode, Au electrode or stainless steel electrode.

8. The method as claimed in claim 6, further comprising an act of pre-storing a function which correlates current and PH values.

9. The method as claimed in claim 6, further comprising an act of receiving data reflecting the type of solution to be detected from a user interface for selecting pre-stored a function from said plurality of functions associated with the type of solution to be detected.

10. The method as claimed in claim 9, wherein the calculating act calculates the PH value of the solution to be detected based on the detected current and the selected pre-stored function.

11. A PH value detection device for detecting the PH value of a solution, comprising:

means for applying a bipolar rectangular potential pulse signal to a first electrode and a second electrode inserted into the solution, wherein the first electrode comprises a transition metal/transition metal oxide electrode, and the second electrode comprises an inert electrode;

means for detecting a current flowing through the first electrode and the second electrode;

means for calculating the PH value of the solution, based on the detected current; and means for pre-storing a plurality of functions correlating current and PH values for a plurality of solution types, each function of the plurality of functions being associated with a type of solution to be detected.

\* \* \* \* \*